United States Patent
Takahashi et al.

(10) Patent No.: US 8,646,310 B2
(45) Date of Patent: Feb. 11, 2014

(54) METHOD FOR DETECTING A GAS CONTAINED IN A FLUID WITH USE OF A GAS SENSOR

(75) Inventors: Kohei Takahashi, Osaka (JP); Tsutomu Kanno, Kyoto (JP); Akihiro Sakai, Osaka (JP); Atsushi Omote, Osaka (JP); Yuka Yamada, Nara (JP)

(73) Assignee: Panasonic Corporation, Osaka (JP)

( * ) Notice: Subject to any disclaimer, the term of this patent is extended or adjusted under 35 U.S.C. 154(b) by 212 days.

(21) Appl. No.: 13/347,484

(22) Filed: Jan. 10, 2012

(65) Prior Publication Data
US 2012/0103067 A1 May 3, 2012

Related U.S. Application Data

(63) Continuation of application No. PCT/JP2011/003372, filed on Jun. 14, 2011.

(30) Foreign Application Priority Data

Oct. 13, 2010 (JP) ................................. 2010-230211

(51) Int. Cl.
*G01N 25/32* (2006.01)
(52) U.S. Cl.
USPC .................... 73/25.05; 73/25.01; 436/144
(58) Field of Classification Search
USPC ...................... 73/25.01, 25.05; 436/144, 147
See application file for complete search history.

(56) References Cited

U.S. PATENT DOCUMENTS

| | | | |
|---|---|---|---|
| 2,234,128 A * | 3/1941 | Miller | 436/152 |
| 7,560,639 B2 | 7/2009 | Kanno et al. | |
| 7,856,874 B2 * | 12/2010 | Tsypko | 73/204.13 |
| 8,475,565 B2 * | 7/2013 | Smith | 95/16 |

(Continued)

FOREIGN PATENT DOCUMENTS

| | | |
|---|---|---|
| JP | 05-259514 | 10/1992 |
| JP | 11-068176 | 3/1999 |

(Continued)

OTHER PUBLICATIONS

Extended Abstracts (The 69th Autumn Meeting, 2008), The Japan Society of Applied Physics, No. 1, p. 215, 2008.

(Continued)

*Primary Examiner* — Lisa Caputo
*Assistant Examiner* — Punam Roy
(74) *Attorney, Agent, or Firm* — McDermott Will & Emery LLP

(57) ABSTRACT

A gas sensor includes a catalyst layer and a pipe-shaped thermoelectric power generation device. The pipe-shaped thermoelectric power generation device includes an internal through-hole along the axial direction of the pipe-shaped thermoelectric power generation device, a plurality of first cup-shaped components each made of metal, a plurality of second cup-shaped components each made of thermoelectric material, and first and second electrodes disposed at the ends of the pipe-shaped power generation device. The plurality of the first cup-shaped components and the plurality of the plurality of second cup-shaped components are arranged alternately and repeatedly along the axial direction. The catalyst layer is arranged on the internal surface of the internal through-hole. A method for detecting or measuring gas by using the gas sensor includes supplying a fluid containing the gas into the internal through-hole of the gas sensor, and detecting voltage between the first and second electrodes.

14 Claims, 17 Drawing Sheets

(56) References Cited

U.S. PATENT DOCUMENTS

| | | | |
|---|---|---|---|
| 2003/0056570 A1* | 3/2003 | Shin et al. | 73/25.05 |
| 2006/0131186 A1* | 6/2006 | Ito et al. | 205/782 |
| 2007/0082310 A1* | 4/2007 | Norton et al. | 431/354 |
| 2008/0053193 A1* | 3/2008 | Ahmad | 73/25.01 |
| 2008/0053194 A1* | 3/2008 | Ahmad | 73/25.01 |
| 2008/0303375 A1 | 12/2008 | Carver | |
| 2010/0170551 A1 | 7/2010 | Hiroyama et al. | |

FOREIGN PATENT DOCUMENTS

| | | |
|---|---|---|
| JP | 2005-098844 | 4/2005 |
| JP | 2005-098845 | 4/2005 |
| JP | 4002969 | 11/2007 |
| JP | 2010-245492 | 10/2010 |
| WO | WO 2008/065799 A1 | 6/2008 |
| WO | WO 2008/150006 A1 | 12/2008 |

OTHER PUBLICATIONS

Tsutomu Kanno, "Thermoelectric Transducer via Off-Diagonal Thermoelectric Effect," Panasonic Technical Journal, vol. 56, No. 2, pp. 122-127, 2010.

International Search Report issued in International Patent Application No. PCT/JP2011/003372, filed Jun. 14, 2011.

\* cited by examiner

METHOD FOR DETECTING A GAS CONTAINED IN A FLUID WITH USE OF A GAS SENSOR

This application is a continuation of PCT/JP2011/003372 filed on Jun. 14, 2011, which claims foreign priority of JP 2010-230211 filed on Oct. 13, 2010, the entire contents of which are incorporated by reference herein.

TECHNICAL FIELD

The present disclosure relates to a gas sensor and a method for detecting a gas and a concentration of a gas by using the gas sensor.

BACKGROUND

FIG. 17 corresponds to FIG. 1 of Japanese Patent No. 4002969, showing a conventional gas sensor. This gas sensor comprises a thermoelectric conversion element 91 and a catalyst layer 92 arranged thereon on a substrate 93. When gas to be detected is adsorbed on the catalyst layer 92, the catalyst layer 92 generates heat. The thermoelectric conversion element 91 converts the heat into an electric power to detect the gas.

SUMMARY

The purpose of the present disclosure is to provide a novel gas sensor and a method for detecting the gas by utilizing the gas sensor.

Solution to Problem

The present disclosure relates to a gas sensor for detecting gas contained in a fluid and/or measuring concentration of the gas in the fluid. One example of the gas sensor according to the present disclosure includes a tubular device having an internal through-hole, a catalyst layer disposed on the surface of the internal through hole, and first and second electrode disposed at ends of the tubular device, respectively. The tubular device includes a plurality of thermoelectric material layers each sandwiched by metal layers, thereby forming power generating units. The plurality of power generating units are connected in series in the tubular device. The thermoelectric material layer is disposed in the tubular device so that at a cross section including the thermoelectric material layer, the catalyst layer, one of adjacent metal layers, the thermoelectric material layers and the other one of the adjacent metal layers are stacked in this order. For example, the thermoelectric material layers are disposed in parallel or are obliquely disposed with respect to the axis direction of the pipe-shaped thermoelectric power generation device.

Another example of the gas sensor includes a catalyst layer and a pipe-shaped thermoelectric power generation device. The pipe-shaped thermoelectric power generation device includes an internal through-hole along the axial direction of the pipe-shaped thermoelectric power generation device, a plurality of first cup-shaped components each made of metal, a plurality of second cup-shaped components each made of thermoelectric material, a first electrode, and a second electrode. The plurality of first cup-shaped components and the plurality of second cup-shaped components are arranged alternately and repeatedly along the axial direction. The first electrode and the second electrode are provided respectively at one end and at the other end of the pipe-shaped thermoelectric power generation device.

Each of the first cup-shaped components has an internal surface and an external surface. Each of the first cup-shaped components also has a first through-hole at a bottom end thereof. A cross sectional area of each of the first cup-shaped components decreases toward the bottom end thereof.

Each of the second cup-shaped components has an internal surface and an external surface. Each of the second cup-shaped components also has a second through-hole at a bottom end thereof. A cross sectional area of each of the second cup-shaped components decreases in the direction toward the bottom end thereof.

When the plurality of first and second cup-shaped components are stacked, the plurality of first through-holes and the plurality of second through-holes constitute the internal through-hole.

Each of the first cup-shaped components is inserted in one adjacent second cup-shaped component in such a manner that the first external surface of each first cup-shaped component is adhered to the second internal surface of the one adjacent second cup-shaped component. The other adjacent second cup-shaped component is inserted in each first cup-shaped component in such a manner that the first internal surface of each first-cup shaped component is adhered to the second external surface of the other adjacent second cup-shaped component. The catalyst layer is arranged on the internal surface of the internal through-hole.

In the above gas sensor, the metal of the pipe-shaped thermoelectric power generation device may be nickel, cobalt, copper, aluminum, silver or gold, or alloy thereof.

In any of the above gas sensor, the thermoelectric material may be Bi, $Bi_2Te_3$, PbTe, or $Bi_2Te_3$ containing Sb or Se.

In any of the above gas sensor, the first external surface of each of the first cup-shaped components may be in contact with the second internal surface of the one adjacent second cup-shaped component, and the first internal surface of each of the first cup-shaped components may be in contact with the second external surface of the other adjacent second cup-shaped component.

In any of the above gas sensor, a conductive material such as a solder may be supplied between the first external surface of each of the first cup-shaped components and the second internal surface of the one adjacent second cup-shaped component. The conductive material may also be supplied between the first internal surface of each of the first cup-shaped components and the second external surface of the other adjacent second cup-shaped component.

In any of the above gas sensor, the following relationships are satisfied:

$$10° \leq \theta_1 \leq 60°,$$

$$10° \leq \theta_2 \leq 60°, \text{ and}$$

$$\theta_1 = \theta_2,$$

where $\theta_1$ represents an angle formed by the internal surface of the first cup-shaped component and the axial direction of the first cup-shaped component (i.e., the smaller angle), and $\theta_2$ represents the angle formed by internal surface of the second cup-shaped component and the axial direction of the second cup-shaped component (i.e., the smaller angel). If $\theta_1$ becomes close to 90° (i.e., the cup-shaped component becomes flat), the voltage appearing between first and second electrodes becomes smaller and sensitivity of the gas sensor decreases. If $\theta_1$ becomes close to 0°, it would be difficult to manufacture the gas sensor.

In any of the above gas sensor, the catalyst layer may be made of platinum, palladium or ceramic containing platinum or palladium. An electrical insulation layer may be interposed between the internal surface of the internal through-hole and the catalyst layer.

In any of the above gas sensor, the ceramic may be made of alumina, tin oxide or zirconia.

The present disclosure also relates to a method for detecting a gas in a fluid and/or measuring concentration of the gas by using any one of the foregoing gas sensor. The method includes steps of (a) preparing any one of the gas sensor as described above, (b) supplying the fluid through the internal through-hole to generate a voltage difference between the first electrode and the second electrode and (c) of detecting the gas contained in the fluid on the basis of the voltage difference. When the concentration of the gas is measured, the concentration of the gas may be measured based on a relationship, for example, a proportional relationship between a concentration and a voltage difference.

Advantageous Effects

The present disclosure provides a novel gas sensor and a method of detecting a gas by utilizing the gas sensor exhibiting higher sensitivity and faster response time.

DETAILED DESCRIPTION

The non-limiting examples of the present subject matter are described below together with the drawings.

The gas sensor according to one example of the present disclosure includes a catalyst layer and a thermoelectric power generating device. The catalyst layer is described later.

Figure 1:
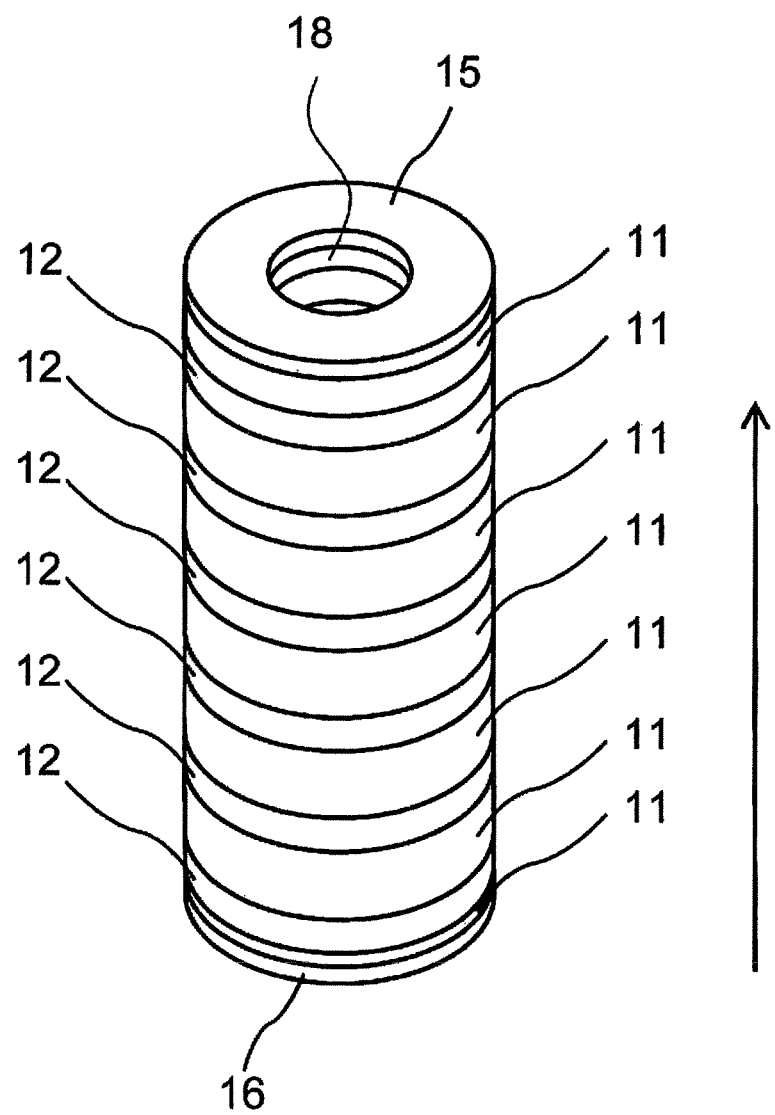
FIG. 1 shows an exemplary view of a pipe-shaped thermoelectric power generating device used in one of the examples of the present disclosure.

FIG. 1 shows a pipe-shaped thermoelectric power generating device. This pipe-shaped thermoelectric power generating device includes an internal through-hole 18, a plurality of first cup-shaped components 11, a plurality of second cup-shaped components 12, a first electrode 15, and a second electrode 16.

The internal through-hole 18 is provided along the axial direction of the pipe-shaped thermoelectric power generating device. The axial direction is the direction indicated by the arrow depicted in FIG. 1.

The first electrode 15 and the second electrode 16 are arranged at one end and at the other end of the pipe-shaped thermoelectric power generating device, respectively.

Each first cup-shaped component 11 is made of metal. An example of the metal is nickel, cobalt, copper, aluminum, silver, gold, or alloy thereof. Nickel, cobalt, copper, or aluminum is preferred.

Each second cup-shaped component 12 is made of thermoelectric conversion material. An example of the thermoelectric conversion material is Bi, $Bi_2Te_3$, or PbTe. When $Bi_2Te_3$ is used, Sb or Se may be contained.

Figure 2:
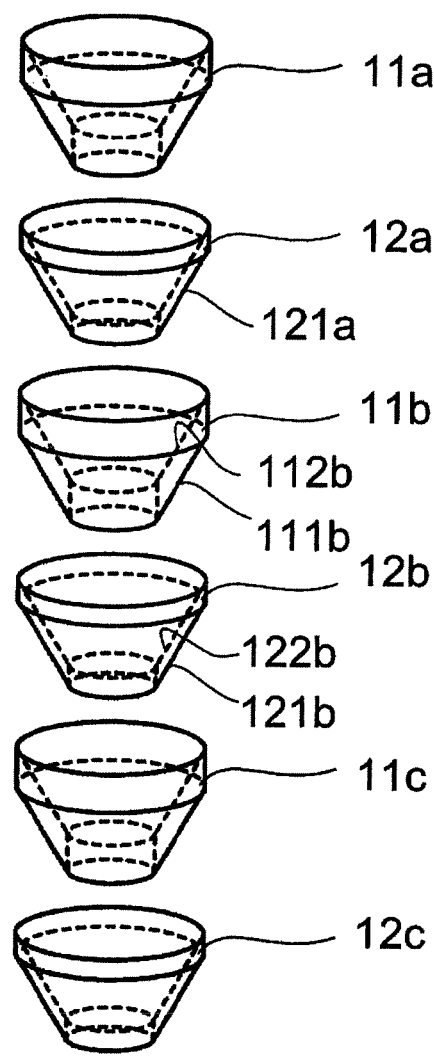
FIG. 2 shows an exemplary partial exploded view of the pipe-shaped thermoelectric power generating device of FIG. 1.

FIG. 2 shows a partial exploded view of the pipe-shaped thermoelectric power generating device. As shown in FIG. 2, three first cup-shaped components $11a$-$11c$ and three second cup-shaped components $12a$-$12c$ are arranged alternately along the axial direction. Each of the first cup-shaped components $11a$-$11c$ has the same shape. Each of the second cup-shaped components $12a$-$12c$ also has the same shape.

Figure 3:
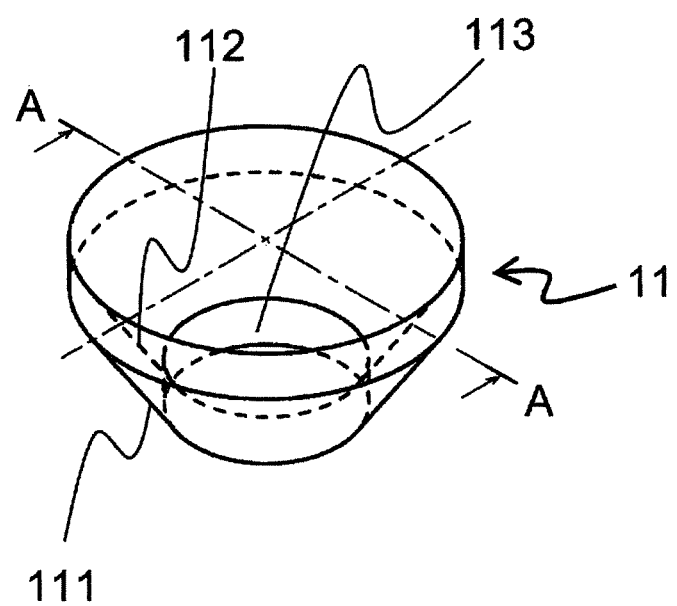
FIG. 3 shows an exemplary view of one of the first cup-shaped components 11.
Figure 4:
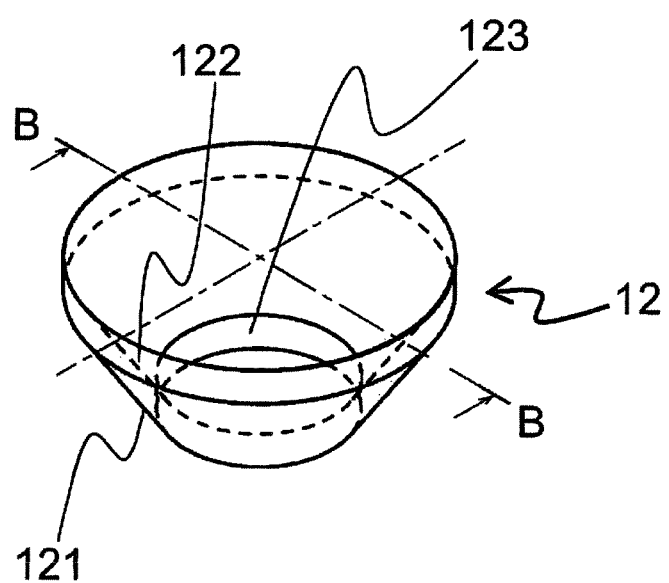
FIG. 4 shows an exemplary view of one of the second cup-shaped components 12.

FIG. 3 shows one of the first cup-shaped components 11. As shown in FIG. 3, the first cup-shaped component 11 has a first inner surface 112 and a first external surface 111. The first cup-shaped component 11 also has a first through-hole 113 at its bottom end. The first cup-shaped component 11 further has an opening at its top end. The cross-sectional area of the first cup-shaped component 11 decreases in a direction toward the bottom of the first cup-shaped component. This cross-sectional area is an area of the cross section of the component cut in a plane perpendicular to a center line of the first through-hole 113. The cross section of the first cup-shaped component 11 shown in FIG. 3 is torus-shaped. The diameter of the first inner surface 112 and the diameter of the first external surface 111 decrease in the direction toward the bottom of the first cup-shaped component. As shown in FIG. 4, similarly to the shape of the first cup-shaped component 11, the second cup-shaped component 12 also has a second inner surface 122, a second external surface 121, and a second through-hole 123. The cross-sectional area of the second cup-shaped component 12 decreases in a direction toward the bottom of the second cup-shaped component. This cross-sectional area is an area of the cross section of the component cut in a plane perpendicular to a center line of the second through-hole 123. The cross section of the second cup-shaped component 12 shown in FIG. 4 is torus-shaped. The diameter of the second inner surface 122 and the diameter of the second external surface 121 decrease in the direction toward the bottom of the first cup-shaped component.

As is clear from FIGS. 1-4, the internal through-hole 18 is composed of the plurality of the first through-holes 113 and the plurality of the second through-holes 123.

As shown in FIG. 2, the first cup-shaped component 11b is inserted into one adjacent second cup-shaped component 12b in such a manner that the first external surface 111b of the first cup-shaped component 11b is adhered to the second internal surface 122b of the one adjacent second cup-shaped component 12b.

The other adjacent second cup-shaped component 12a is inserted into the first cup-shaped component 11b in such a manner that the first internal surface 112b of the first cup-shaped component 11b is adhered to the second external surface 121a of the other adjacent second cup-shaped component 12a.

In this manner, one first cup-shaped component 11 is adhered to two adjacent second cup-shaped components 12. Similarly, one second cup-shaped component 12 is also adhered to two adjacent first cup-shaped components 11.

It is preferable that the external surface 111b of the first cup-shaped component 11b is in directly contact with the second internal surface 122b of the one adjacent second cup-shaped component 12b. Instead of the direct contact, these surfaces may be adhered by a conductive material such as a solder supplied between the external surface 111b of the first cup-shaped component 11b and the second internal surface 122b of the one adjacent second cup-shaped component 12b.

Similarly to the above, it is preferable that the internal surface 112b of the first cup-shaped component 11b is in direct contact with the second external surface 121a of the other adjacent second cup-shaped component 12a. Instead of the direct contact, these surfaces may be adhered by a conductive material such as a solder supplied therebetween.

It is preferable not to have gap or space between the first cup-shaped component 11 and the adjacent second cup-shaped component 12, since the gap or space may prevent thermoelectric conversion when fluid is flowed through the internal through-hole 18, as described later. Furthermore, the fluid may leak out from the gap or space. A conductive adhesive material such as solder may be filled into the gap or space optionally, as described above.

The numbers of the first cup-shaped component 11 and the second cup-shaped component 12 are, for example, but are not limited to not less than 100 and not more than 1000.

Figure 5:
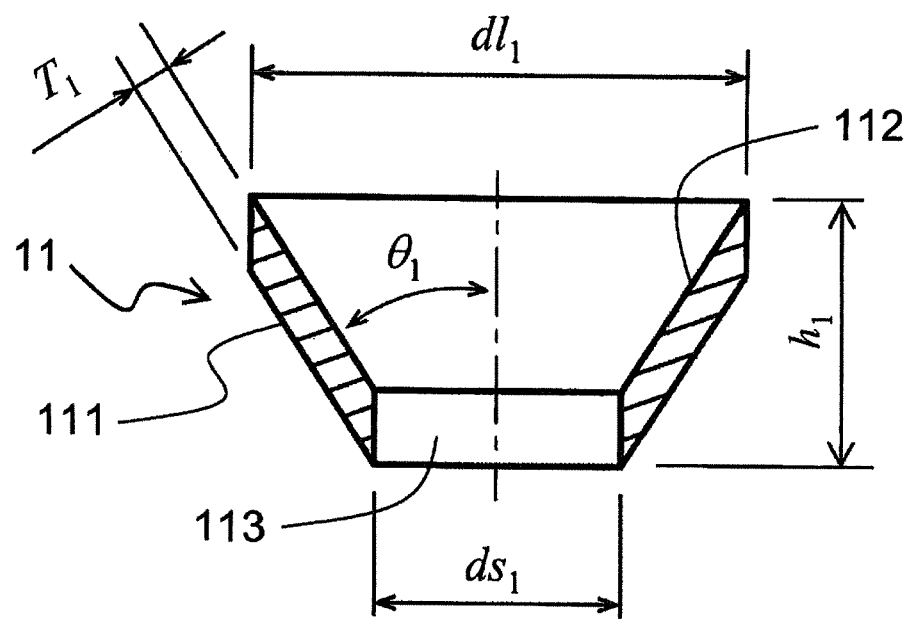
FIG. 5 shows an exemplary cross-sectional view of the A-A line depicted in FIG. 3.
Figure 6:
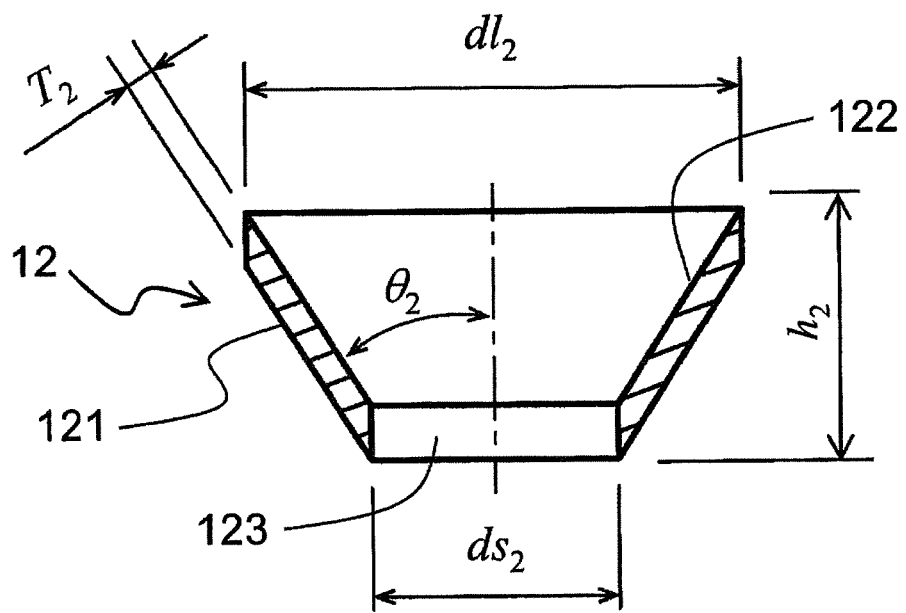
FIG. 6 shows an exemplary cross-sectional view of the B-B line depicted in FIG. 4.

FIG. 5 shows a cross-sectional view of the A-A line depicted in FIG. 3. FIG. 6 shows a cross-sectional view of the B-B line depicted in FIG. 4. Angles $\theta_1$ and $\theta_2$ represent gradient angels of the first internal surface 112 of the first cup-shaped component 11 and the second internal surface 122 of the second cup-shaped component 12, respectively. Namely, $\theta_1$ represents the angle formed by the portion where the cross-sectional area of the first cup-shaped component 11 is decreased in the direction of its bottom end and the axial direction of the first cup-shaped component 11. Similarly, $\theta_2$ represents the angle formed by the portion where the cross-sectional area of the second cup-shaped component 12 is decreased in the direction of its bottom end and the axial direction of the second cup-shaped component 12. The value of $\theta_1$ is equal to the value of $\theta_2$. The preferable values of $\theta_1$ and $\theta_2$ are not less than 10° and not more than 60°.

The cross-sectional shape of the internal through-hole 18 is not limited. The cross-sectional shape of the pipe-shaped thermoelectric power generating device is not limited, either.

When the cross-sectional shape of the first cup-shaped component 11 is a circle, $dl_1$ and $ds_1$ shown in FIG. 5 represent the widths of the top and bottom ends of the first cup-shaped component 11, respectively. The first cup-shaped component 11 has a height $h_1$ and a thickness $T_1$. Similarly to the case of FIG. 5, $dl_2$, $ds_2$, $h_2$, and $T_2$ shown in FIG. 6 represent a top end width, a bottom end width, a height, and a thickness of the second cup-shaped component 12, respectively. Preferably, the thickness $T_1$ and the thickness $T_2$ are each 0.1 to 0.5 mm.

The cross-sectional shape of the pipe-shaped thermoelectric power generating device is not limited. An example of the cross-sectional shape of the pipe-shaped thermoelectric power generating device is a circle, an ellipse, or a polygon. A circle is preferred. Namely, it is preferable that the pipe-shaped thermoelectric power generating device is cylindrical.

Figure 7:
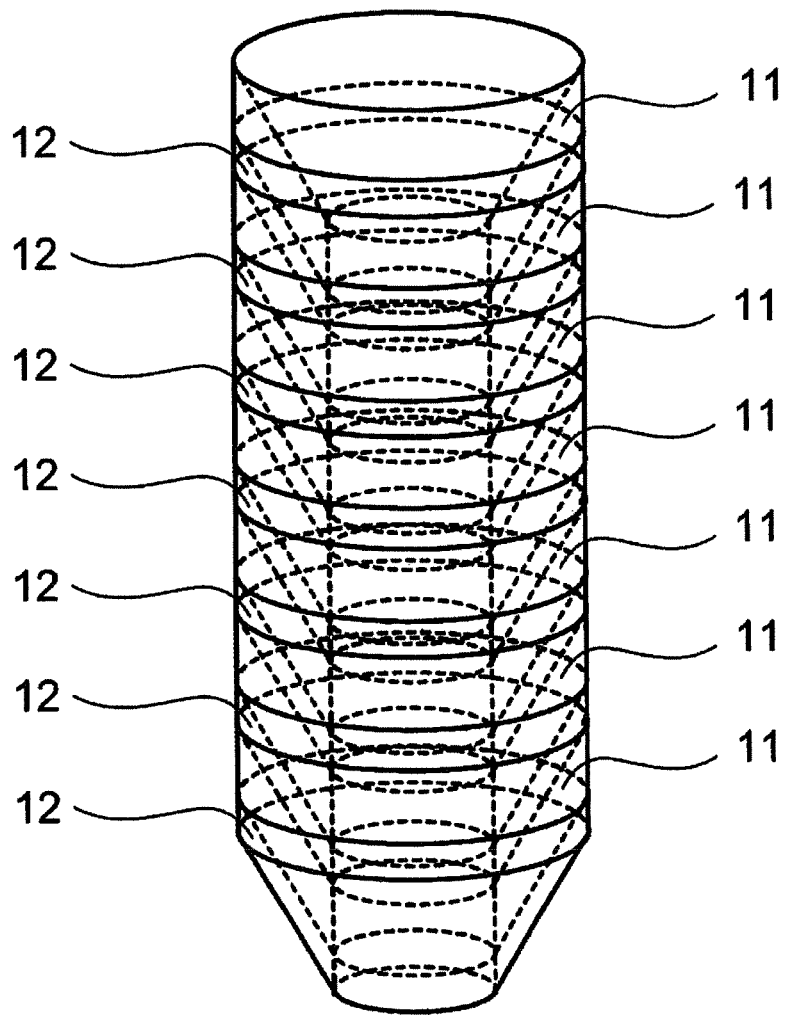
FIG. 7 shows an exemplary view of one step in a method for fabricating the pipe-shaped thermoelectric power generating device.
Figure 8:
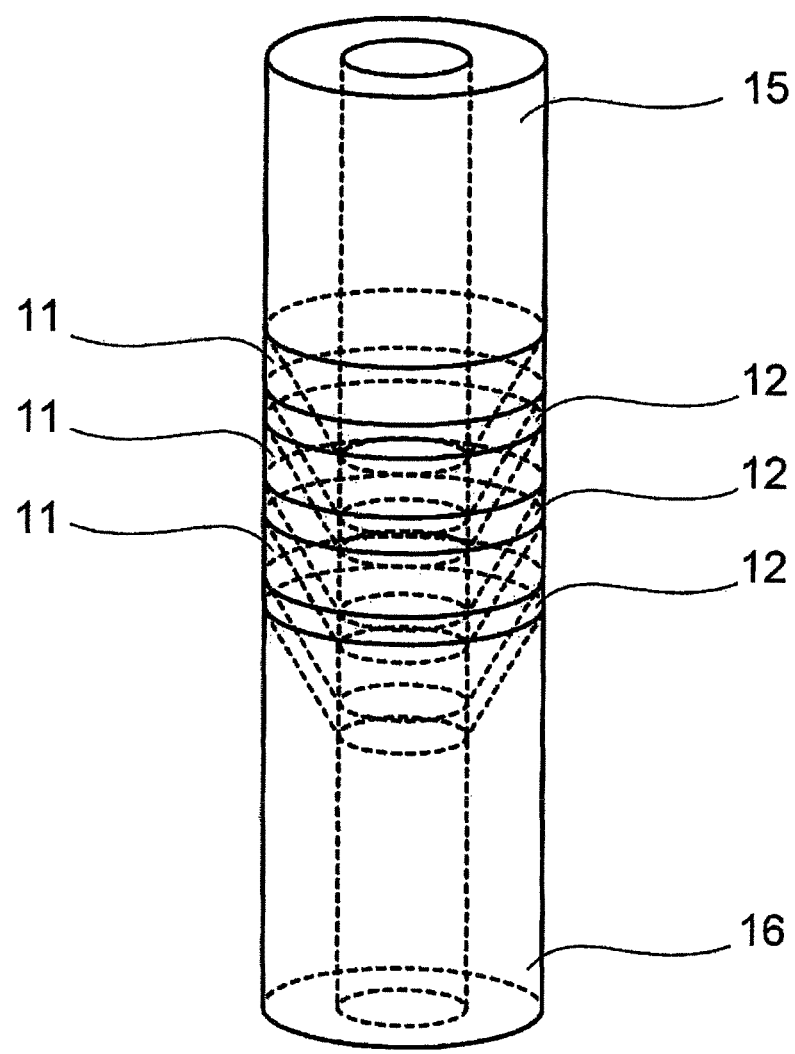
FIG. 8 shows an exemplary view of one step in the method for fabricating the pipe-shaped thermoelectric power generating device.
Figure 9:
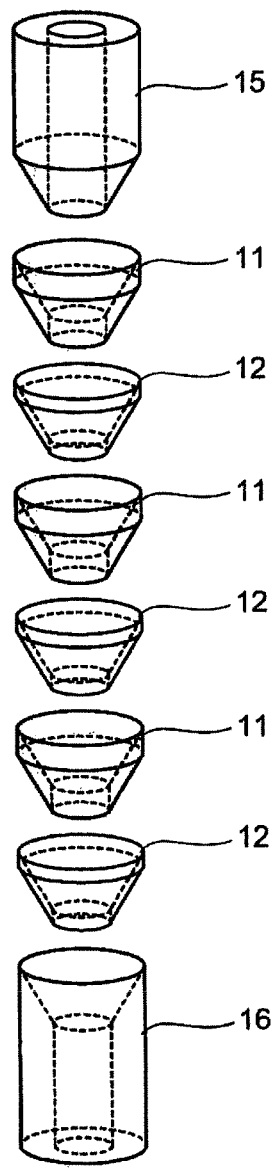
FIG. 9 shows an exploded view of the pipe-shaped thermoelectric power generating device shown in FIG. 8.

As shown in FIG. 7, a plurality of the first cup-shaped components 11 and a plurality of the second cup-shaped components 12 are arranged alternately and repeatedly. Subsequently, as shown in FIG. 8 and FIG. 9, the first electrode 15 and the second electrode 16 are joined at the end thereof and at the other end thereof, respectively, so as to obtain a pipe-shaped thermoelectric power generation device. FIG. 9 is an exploded view of FIG. 8.

Figure 10:
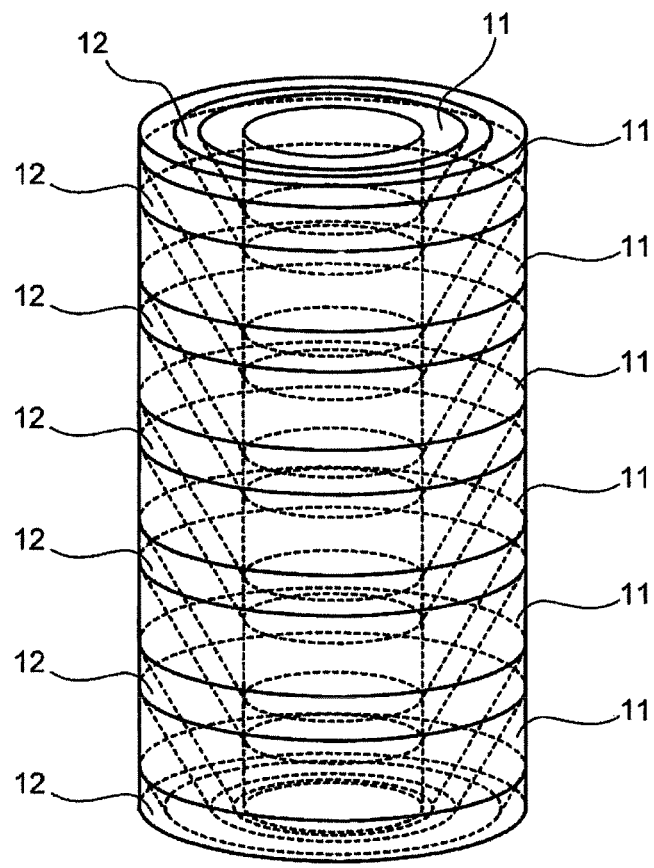
FIG. 10 shows an exemplary view of one step in another method for fabricating the pipe-shaped thermoelectric power generating device.
Figure 11:
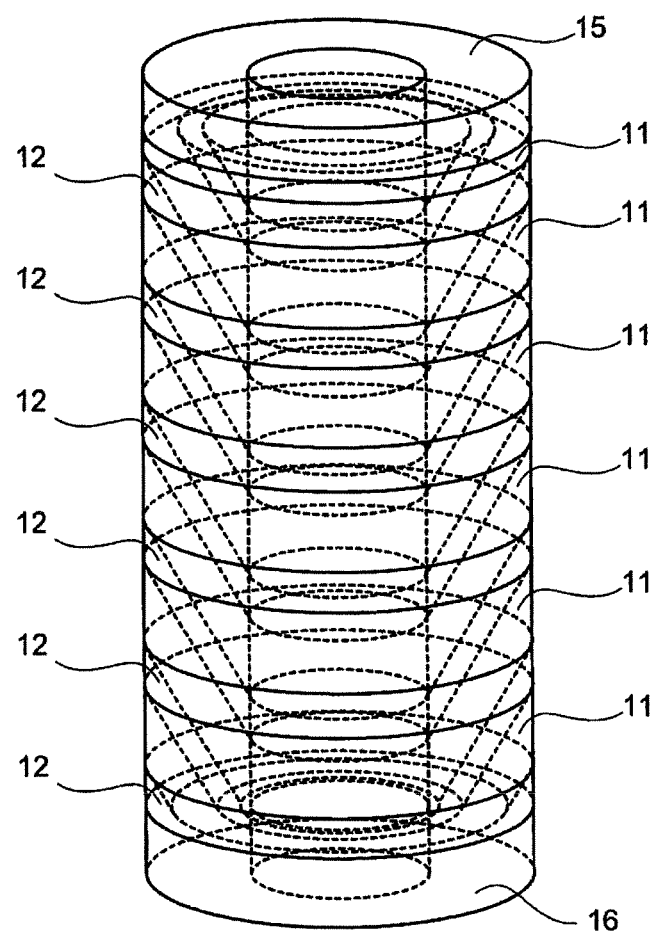
FIG. 11 shows an exemplary view of one step in another method for fabricating the pipe-shaped thermoelectric power generating device.

Instead of the procedures shown in FIG. 8 and FIG. 9, the first electrode 15 and the second electrode 16 may be joined as described below. After the process as shown in FIG. 7, a part of the one end and a part of the other end are cut off to cause the one end and the other end to be flat, as shown in FIG. 10. Subsequently, the plate-like first electrode 15 and the plate-like second electrode 16 are joined to the one end and the other end, respectively, so as to obtain a pipe-shaped thermoelectric power generation device.

Figure 13:
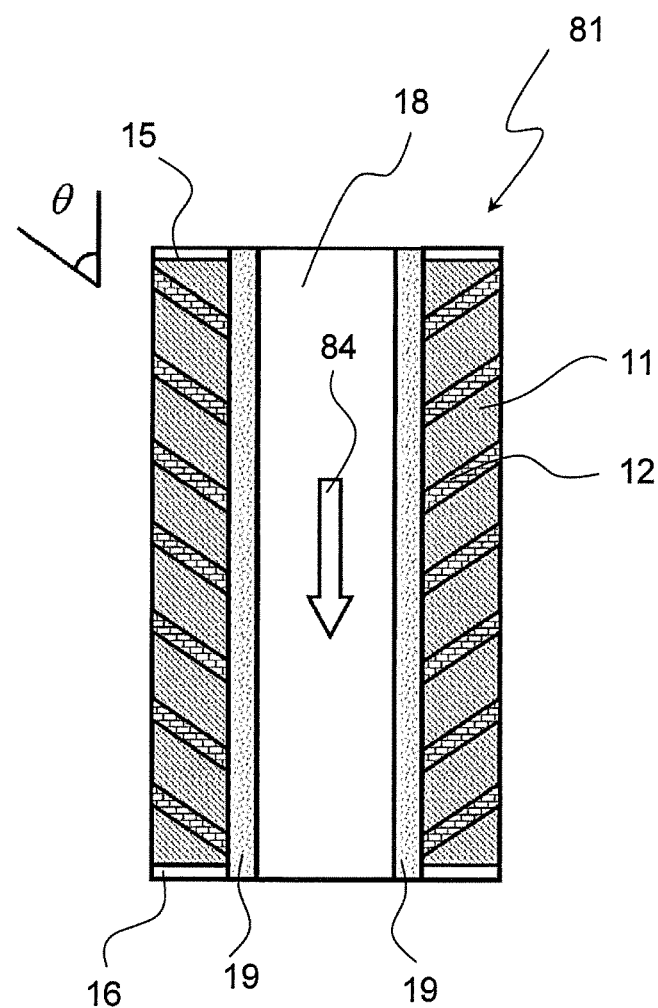
FIG. 13 shows an exemplary cross-sectional view of a gas sensor according to one example the present disclosure.

The gas sensor comprising such a pipe-shaped thermoelectric power generation device is described below with reference to FIG. 13. FIG. 13 shows a cross-sectional view of the pipe-shaped thermoelectric power generation device shown in FIG. 1.

As shown in FIG. 13, a catalyst layer 19 is arranged on the internal surface of the internal through-hole 18 of the pipe-shaped thermoelectric power generation device. In FIG. 13, the internal surface of the internal through-hole 18 is coated with the catalyst layer 19. It is not necessary that the entirety of the internal surface of the internal through-hole 18 is covered with the catalyst layer 19. In other words, a portion of the internal surface of the internal through-hole 18 may be covered with the catalyst layer 19.

When a gas to be detected or measured is hydrogen, the catalyst layer 19 is made of ceramic containing platinum or palladium. An example of the preferred material of the ceramic is alumina.

When a gas to be detected or measured is CO or $N\theta_R$, the catalyst layer 19 is made of ceramic containing platinum or palladium. An example of the preferred material of the ceramic is tin oxide or zirconia.

Figure 14:
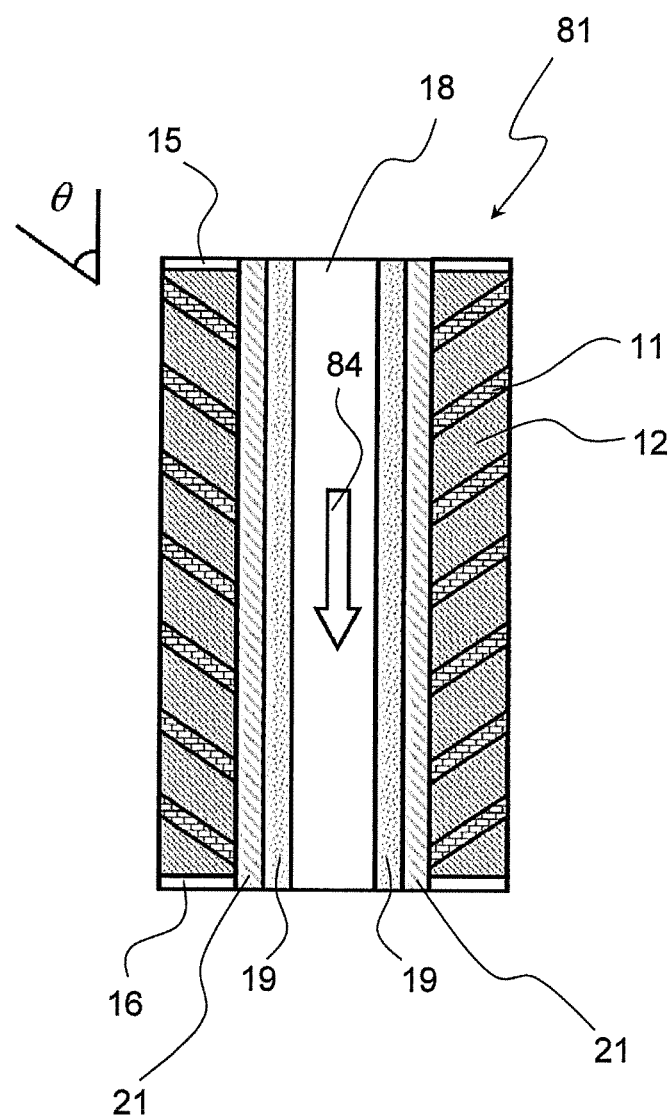
FIG. 14 shows an exemplary cross-sectional view of another gas sensor according to another example of the present disclosure.

When a gas to be detected or measured is hydrogen, the catalyst layer 19 is made of a platinum layer or a palladium layer. In this case, as shown in FIG. 14, an electric insulation layer 21 is interposed between the internal surface of the internal through-hole 18 and the catalyst layer 19.

The catalyst layer 19 may be heated by a heater to increase activity of the catalyst layer 19. This improves accuracy of detection and concentration measurement of the gas. The heater may be arranged inside or outside the internal through-hole 18.

Next, a method for detecting gas with use of the gas sensor is described below.

Figure 15:
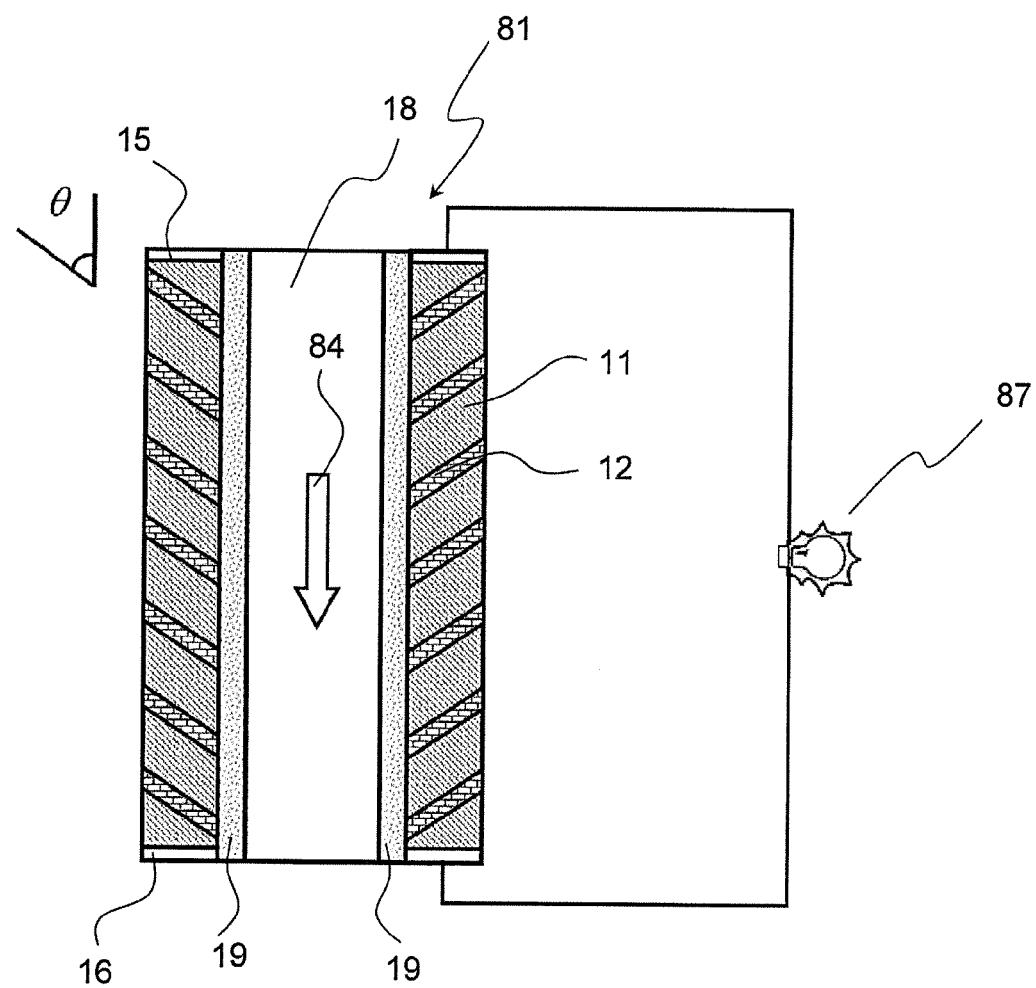
FIG. 15 shows a gas detector using the gas sensor according to one example of the present disclosure.

As shown in FIG. 15, a fluid 84 containing the gas to be detected is flowed through the internal through-hole 18. The gas is adsorbed on the catalyst layer 19, and the catalyst layer 19 generates heat. As a result, a heat difference is generated between the internal surface and the external surface of the pipe-shaped thermoelectric power generation device 81. The heat difference is converted to a voltage difference between the first electrode 15 and the second electrode 16 by the pipe-shaped thermoelectric power generation device. The thermoelectric layer of second cup-shaped component generates a potential difference due to the heat difference between the both sides of the thermoelectric layer. Since the first and second cup-shaped components are connected in series, the first and second electrode output a voltage. Thus, if the fluid 84 contains the gas to be detected, the voltage difference is generated between the first electrode 15 and the second electrode 16. On the contrary, if the fluid 84 does not contains the gas to be detected, the voltage difference is not generated between the first electrode 15 and the second electrode 16.

In FIG. 15, an electric lamp 87 is electrically connected between the first electrode 15 and the second electrode 16. The voltage difference turns on the electric lamp 87. Instead of the electric lamp 87, an LED, a potentiometer or a buzzer may be used. The electric lamp 87 or the buzzer serves as a notification unit. A gas detector according to the present disclosure may include the gas sensor and the notification unit.

A method for measuring concentration of the gas contained in the fluid with use of the gas sensor is described below.

Figure 16:
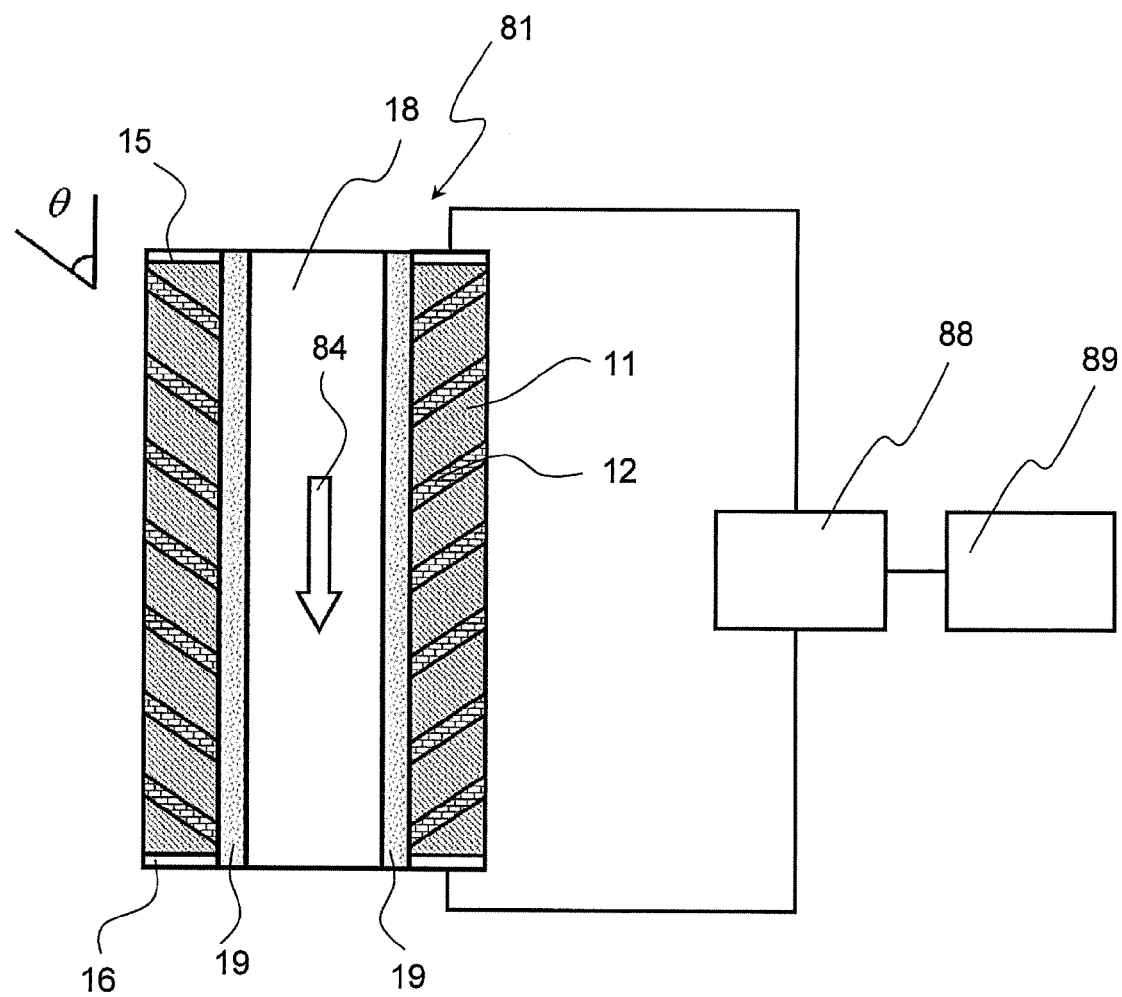
FIG. 16 shows a gas concentration measurement device using the gas sensor according to one example of the present disclosure.

As shown in FIG. 16, a gas concentration measurement instrument according to the present disclosure includes a memory unit 89, a processing unit 88, and the gas sensor 81. Similar to the case of FIG. 15, the fluid 84 is flowed through the internal through-hole 18 and a voltage difference is generated when the fluid includes the gas to be measured. As is clear from the examples described later, the applicants discovered a relationship that the voltage difference is proportional to the concentration of the gas. The relationship (e.g., proportionality coefficient) is stored in the memory unit 89, for example, a ROM. The processing unit 88, for example, a processor or a microcomputer, is electrically connected to the first electrode 15 and the second electrode 16. The processing unit 88 calculates the concentration of the gas on the basis of the voltage difference generated therebetween with reference to the memory unit 89. The concentration of the gas thus calculated may be output to a display or a speaker (neither of which is shown). The voltage difference may be directly converted to the gas concentration without referring to the memory unit.

Figure 12:
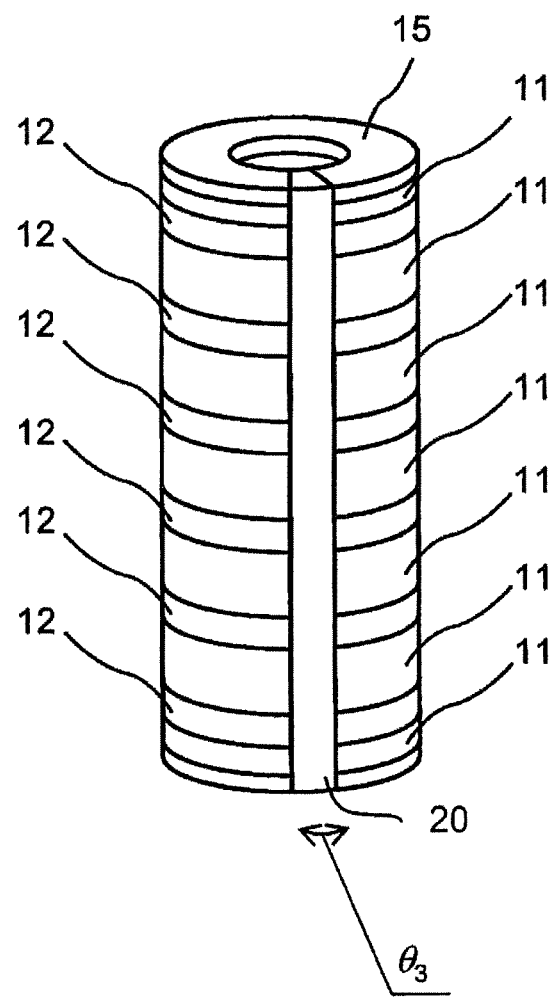
FIG. 12 shows an exemplary view of another example of a pipe-shaped thermoelectric power generating device.

As shown in FIG. 12, a groove 20 may be formed along the axial direction in the pipe-shaped thermoelectric power generation devices 81. The groove 20 may be hollow, and may be filled with insulator optionally. The angel of $\theta_3$ of the groove 20 is preferably not less than 1 degree and not more than 10 degrees.

EXAMPLES

The present subject matter is described in more detail with reference to the following examples.

Example 1A

In accordance with Table 1, the pipe-shaped thermoelectric power generation device 81 shown in FIG. 9 was obtained.

TABLE 1

| | |
|---|---|
| Material of the first cup-shaped component 11 | Copper |
| The number of the first cup-shaped component 11 | 199 |
| $dl_1$ | 7 millimeters |
| $ds_1$ | 5 millimeters |
| $h_1$ | 4 millimeters |
| $\theta_1$ | 10 degrees |
| Material of the second cup-shaped component 12 | $Bi_2Te_3$ |
| The number of the second cup-shaped component 12 | 200 |
| $dl_2$ | 7 millimeters |
| $ds_2$ | 5 millimeters |
| $h_2$ | 3.2 millimeters |
| $\theta_2$ | 10 degrees |
| Material of the first electrode 15 and the second electrode 16 | copper |

Each end part of the pipe-shaped thermoelectric power generation device 81 was tightened up with a nut. A spring made of inconel alloy was inserted between the nut and the first electrode 15. While the pipe-shaped thermoelectric power generation device 81 was compressed by the spring along the axial direction, the pipe-shaped thermoelectric power generation device 81 was placed into a tubular oven. The pipe-shaped thermoelectric power generation device 81 was heated at 500 degrees Celsius for two hours.

After heated, the pipe-shaped thermoelectric power generation device 81 was cooled to room temperature. Thus, obtained was the pipe-shaped thermoelectric power generation device 81 having an external diameter of approximately 7 millimeters, an internal diameter of approximately 5 millimeters, and a length of 500 millimeters. The obtained pipe-shaped thermoelectric power generation device 81 was cut into five portions. Each portion had a length of 100 millimeters.

Alumina powder was added to a platinum chloride aqueous solution to prepare a catalyst solution. The catalyst solution was added to ethanol to prepare a paste. The paste was applied to the internal surface of the internal through-hole 18. Subsequently, the pipe-shaped thermoelectric power generation device 81 thus obtained was sintered at 200 degrees Celsius to obtain the gas sensor.

A gas mixture of hydrogen and nitrogen was supplied to the internal through-hole 18, and the voltage difference generated between the first electrode 15 and the second electrode 16 was measured with a nano-voltmeter. The following Table 2 shows the concentration of the hydrogen and the generated voltage difference.

Examples 1B-1C

The experiments identical to the example 1A were performed except for $\theta_1=\theta_2=30°$ or 60°.

TABLE 2

| | Hydrogen Concentration (%) | | | | | |
|---|---|---|---|---|---|---|
| | 0.001 | 0.01 | 0.1 | 0.5 | 1 | 3 |
| Example 1A ($\theta = 10°$) | 16 μV | 0.16 mV | 1.6 mV | 4.5 mV | 9.8 mV | 28 mV |
| Example 1B ($\theta = 30°$) | 7.2 μV | 70 μV | 0.7 mV | 2.0 mV | 4.3 mV | 12 mV |
| Example 1C ($\theta = 60°$) | 2.4 μV | 25 μV | 0.25 mV | 0.7 mV | 1.5 mV | 4.3 mV |

As is clear from Table 2, the voltage difference was substantially proportional to the concentration of the hydrogen.

In addition, the voltage appearing between the first and second electrode were high when the angle θ is small.

A response time of the gas sensors prepared in the examples 1A-1C were measured. Table 3 shows the results. The response time was calculated by the following equation:

(Response time)=time required from the beginning of the measurement to the time point when the voltage difference is equal to 63.2% of the voltage difference generated in a steady state.

According to the experience conducted by the present inventors, the response time had no relationship to the concentration of the hydrogen.

TABLE 3

|  | Example 1A | Example 1B | Example 1C |
|---|---|---|---|
| Response time (Second) | 4.5 | 1.5 | 0.5 |

As is clear from Table 3, the response time was a significantly short time of 4.5 seconds or less.

Examples 2A-2C

In accordance with Table 4, the gas sensors were obtained similarly to the case of the examples 1A-1C. Unlike the examples 1A-1C, the material of the first cup-shaped component 11 was nickel in the examples 2A-2C. Table 5 and Table 6 show the results.

TABLE 4

| | |
|---|---|
| Material of the first cup-shaped component 11 | Nickel |
| The number of the first cup-shaped component 11 | 199 |
| $dl_1$ | 7 millimeters |
| $ds_1$ | 5 millimeters |
| $H_1$ | 4 millimeters |
| $\theta_1$ | 10 degrees |
| Material of the second cup-shaped component 12 | $Bi_2Te_3$ |
| The number of the second cup-shaped component 12 | 200 |
| $dl_2$ | 7 millimeters |
| $ds_2$ | 5 millimeters |
| $h_2$ | 3.2 millimeters |
| $\theta_2$ | 10 degrees |
| Material of the first electrode 15 and the second electrode 16 | copper |

TABLE 5

| | Hydrogen Concentration (%) | | | | | |
|---|---|---|---|---|---|---|
| | 0.001 | 0.01 | 0.1 | 0.5 | 1 | 3 |
| Example 2A (θ = 10°) | 35 μV | 0.35 mV | 3.5 mV | 9.7 mV | 21 mV | 62 mV |
| Example 2B (θ = 30°) | 28 μV | 0.27 μV | 2.8 mV | 7.7 mV | 16 mV | 49 mV |
| Example 2C (θ = 60°) | 11 μV | 0.11 mV | 1.1 mV | 3.0 mV | 6.6 mV | 19 mV |

TABLE 6

|  | Example 2A | Example 2B | Example 2C |
|---|---|---|---|
| Response time (Second) | 4.5 | 1.5 | 0.5 |

Examples 3A-3C

In accordance with Table 7, the gas sensors were obtained similarly to the case of the examples 1A-1C. Unlike the examples 1A-1C, the material of the second cup-shaped component 12 was PbTe in the examples 3A-3C. Table 8 and Table 9 show the results.

TABLE 7

| | |
|---|---|
| Material of the first cup-shaped component 11 | Copper |
| The number of the first cup-shaped component 11 | 199 |
| $dl_1$ | 7 millimeters |
| $ds_1$ | 5 millimeters |
| $h_1$ | 4 millimeters |
| $\theta_1$ | 10 degrees |
| Material of the second cup-shaped component 12 | PbTe |
| The number of the second cup-shaped component 12 | 200 |
| $dl_2$ | 7 millimeters |
| $ds_2$ | 5 millimeters |
| $h_2$ | 3.2 millimeters |
| $\theta_2$ | 10 degrees |
| Material of the first electrode 15 and the second electrode 16 | copper |

TABLE 8

| | Hydrogen Concentration (%) | | | | | |
|---|---|---|---|---|---|---|
| | 0.001 | 0.01 | 0.1 | 0.5 | 1 | 3 |
| Example 3A (θ = 10°) | 21 μV | 0.21 mV | 2.1 mV | 5.9 mV | 13 mV | 37 mV |
| Example 3B (θ = 30°) | 10 μV | 0.11 mV | 1.1 mV | 2.9 mV | 6.3 mV | 18 mV |
| Example 3C (θ = 60°) | 38 μV | 37 μV | 0.37 mV | 1.0 mV | 2.3 mV | 6.5 mV |

TABLE 9

|  | Example 3A | Example 3B | Example 3C |
|---|---|---|---|
| Response time (Second) | 1.0 | Less than 0.5 | Less than 0.5 |

Examples 4A-4C

In accordance with Table 10, the gas sensors were obtained similarly to the case of the examples 1A-1C. Unlike the examples 1A-1C, the materials of the first and second cup-shaped components were nickel and PbTe, respectively, in the examples 4A-4C. Table 11 and Table 12 show the results.

TABLE 10

| | |
|---|---|
| Material of the first cup-shaped component 11 | Nickel |
| The number of the first cup-shaped component 11 | 199 |
| $dl_1$ | 7 millimeters |
| $ds_1$ | 5 millimeters |
| $h_1$ | 4 millimeters |
| $\theta_1$ | 10 degrees |
| Material of the second cup-shaped component 12 | PbTe |
| The number of the second cup-shaped component 12 | 200 |
| $dl_2$ | 7 millimeters |
| $ds_2$ | 5 millimeters |

TABLE 10-continued

| | |
|---|---|
| $h_2$ | 3.2 millimeters |
| $\theta_2$ | 10 degrees |
| Material of the first electrode 15 and the second electrode 16 | copper |

TABLE 11

| | Hydrogen Concentration (%) | | | | | |
|---|---|---|---|---|---|---|
| | 0.001 | 0.01 | 0.1 | 0.5 | 1 | 3 |
| Example 4A ($\theta = 10°$) | 40 µV | 0.4 mV | 4 mV | 11 mV | 24 mV | 70 mV |
| Example 4B ($\theta = 30°$) | 37 µV | 0.38 mV | 3.8 mV | 10.5 mV | 23 mV | 67 mV |
| Example 4C ($\theta = 60°$) | 13 µV | 0.15 mV | 1.6 mV | 4.4 mV | 9.5 mV | 28 mV |

TABLE 12

| | Example 4A | Example 4B | Example 4C |
|---|---|---|---|
| Response time (Second) | 2.5 | 1.0 | Less than 0.5 |

Examples 5A-5C

In accordance with Table 13, the gas sensors were obtained similarly to the case of the examples 1A-1C. Unlike the examples 1A-1C, the material of the second cup-shaped component 12 was bismuth in the examples 5A-5C. Table 14 and Table 15 show the results.

TABLE 13

| | |
|---|---|
| Material of the first cup-shaped component 11 | Copper |
| The number of the first cup-shaped component 11 | 199 |
| $dl_1$ | 7 millimeters |
| $ds_1$ | 5 millimeters |
| $h_1$ | 4 millimeters |
| $\theta_1$ | 10 degrees |
| Material of the second cup-shaped component 12 | Bismuth |
| The number of the second cup-shaped component 12 | 200 |
| $dl_2$ | 7 millimeters |
| $ds_2$ | 5 millimeters |
| $h_2$ | 3.2 millimeters |
| $\theta_2$ | 10 degrees |
| Material of the first electrode 15 and the second electrode 16 | copper |

TABLE 14

| | Hydrogen Concentration (%) | | | | | |
|---|---|---|---|---|---|---|
| | 0.001 | 0.01 | 0.1 | 0.5 | 1 | 3 |
| Example 5A ($\theta = 10°$) | 2.3 µV | 25 µV | 0.26 mV | 0.7 mV | 1.5 mV | 4.5 mV |
| Example 5B ($\theta = 30°$) | 2.0 µV | 21 µV | 0.22 mV | 0.6 mV | 1.3 mV | 3.8 mV |
| Example 5C ($\theta = 60°$) | 8.4 µV | 87 µV | 88 µV | 0.24 mV | 0.5 mV | 1.5 mV |

TABLE 15

| | Example 5A | Example 5B | Example 5C |
|---|---|---|---|
| Response time (second) | Less than 0.5 | Less than 0.5 | Less than 0.5 |

Examples 6A-6C

In accordance with Table 16, the gas sensors were obtained similarly to the case of the examples 1A-1C. Unlike the examples 1A-1C, the materials of the first and second cup-shaped components were nickel and bismuth, respectively, in the examples 6A-6C. Table 17 and Table 18 show the results.

TABLE 16

| | |
|---|---|
| Material of the first cup-shaped component 11 | Nickel |
| The number of the first cup-shaped component 11 | 199 |
| $dl_1$ | 7 millimeters |
| $ds_1$ | 5 millimeters |
| $h_1$ | 4 millimeters |
| $\theta_1$ | 10 degrees |
| Material of the second cup-shaped component 12 | Bismuth |
| The number of the second cup-shaped component 12 | 200 |
| $dl_2$ | 7 millimeters |
| $ds_2$ | 5 millimeters |
| $h_2$ | 3.2 millimeters |
| $\theta_2$ | 10 degrees |
| Material of the first electrode 15 and the second electrode 16 | copper |

TABLE 17

| | Hydrogen Concentration (%) | | | | | |
|---|---|---|---|---|---|---|
| | 0.001 | 0.01 | 0.1 | 0.5 | 1 | 3 |
| Example 6A ($\theta = 10°$) | 2.3 µV | 25 µV | 0.24 mV | 0.66 mV | 1.4 mV | 4.2 mV |
| Example 6B ($\theta = 30°$) | 4.0 µV | 41 µV | 0.4 mV | 1.1 mV | 2.4 mV | 7 mV |
| Example 6C ($\theta = 60°$) | 2.2 µV | 21 µV | 0.23 mV | 0.64 mV | 1.3 mV | 3.9 mV |

TABLE 18

| | Example 6A | Example 6B | Example 6C |
|---|---|---|---|
| Response time (second) | 1.0 | 0.5 | Less than 0.5 |

Comparative Example 1

Figure 17:
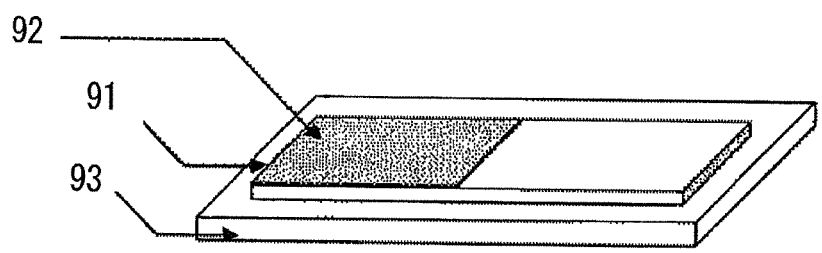
FIG. 17 shows a conventional gas sensor.

A gas sensor was obtained in accordance with the conventional method as described in JP 4002969. More particularly, a SiGe thin film having a thickness of 800 nanometers was formed on an alumina substrate by a sputtering technique. The alumina substrate was 20 millimeters long, 10 millimeters wide, and 0.5 millimeters thick. Indium films were applied to both ends of the SiGe thin film to form electrodes. Furthermore, as shown in FIG. 17, a catalyst layer was applied on the half of the surface of the SiGe thin film. The catalyst layer was formed similarly to that of the example 1A. Table 19 and Table 20 show the property of the gas sensor thus obtained.

TABLE 19

| | Hydrogen Concentration (%) | | | |
|---|---|---|---|---|
| | 0.1 | 0.5 | 1 | 3 |
| Comparative example 1 | 0.9 μV | 30 μV | 0.17 mV | 0.5 mV |

TABLE 20

| | Comparative Example 1 |
|---|---|
| Response time | Approximately 20 second |

A skilled person would understand easily that the gas sensors according to the examples 1A-6C are superior to the gas sensor according to the comparative example

INDUSTRIAL APPLICABILITY

The gas sensor according to the present disclosure is used in order to adjust a hydrogen gas concentration, or in order to detect a leakage of hydrogen gas. As one example, the gas sensor is installed in a fuel cell.

REFERENCE SIGNS LIST 11 first cup-shaped component
111 first external surface
112 first internal surface
113 first through-hole
12 second cup-shaped component
121 second external surface
122 second internal surface
123 second through-hole
15 first electrode
16 second electrode
18 internal through-hole
19 catalyst layer
20 groove
21 electric insulation layer
81 pipe-shaped thermoelectric power generation device
87 electric lamp
88 processing unit
89 memory unit

What is claimed is:

1. A method for detecting a gas contained in a fluid with use of a gas sensor, the method comprising:
a step (a) of preparing the gas sensor, wherein:
the gas sensor comprises a catalyst layer and a pipe-shaped thermoelectric power generation device,
the pipe-shaped thermoelectric power generation device comprises:
an internal through-hole along an axial direction of the pipe-shaped thermoelectric power generation device;
a plurality of first cup-shaped components each made of metal;
a plurality of second cup-shaped components each made of a thermoelectric material;
a first electrode; and
a second electrode,
the plurality of first cup-shaped components and the plurality of second cup-shaped components are stacked alternately and repeatedly along the axial direction,
the first electrode and the second electrode are provided respectively at one end and at the other end of the pipe-shaped thermoelectric power generation device,
each of the first cup-shaped components has an internal surface and an external surface,
each of the first cup-shaped components comprises a first through-hole at a bottom end thereof,
a cross-sectional area of each of the first cup-shaped components decreases in a direction toward the bottom end thereof,
each of the second cup-shaped components has an internal surface and an external surface,
each of the second cup-shaped components comprises a second through-hole at a bottom end thereof,
a cross-sectional area of each of the second cup-shaped components decreases in a direction toward the bottom end thereof,
the internal through-hole is composed of the plurality of the first through-holes and the plurality of the second through-holes,
each first cup-shaped component is inserted in one adjacent second cup-shaped component in such a manner that the first external surface of each first cup-shaped component is adhered to the second internal surface of the one adjacent second cup-shaped component,
the other adjacent second cup-shaped component is inserted in each first cup-shaped component in such a manner that the first internal surface of each first-cup shaped component is adhered to the second external surface of the other adjacent second cup-shaped component, and
the catalyst layer is disposed on an internal surface of the internal through-hole;
a step (b) of supplying the fluid through the internal through-hole to generate a voltage difference between the first electrode and the second electrode; and
a step (c) of detecting the gas contained in the fluid on the basis of the voltage difference.

2. The method according to claim 1, wherein in the step (c), a concentration of the gas is measured based on a relationship between a concentration and a voltage difference.

3. The method according to claim 1, wherein the relationship is proportional.

4. The method according to claim 1, wherein the metal of the plurality of first cup-shaped components is nickel, cobalt, copper, aluminum, silver or gold, or alloy thereof.

5. The method according to claim 1, wherein the thermoelectric material of the plurality of second cup-shaped components is Bi, $Bi_2Te_3$, PbTe or $Bi_2Te_3$ containing Sb or Se.

6. The method according to claim 1, wherein:
the first external surface of each first cup-shaped component is in contact with the second internal surface of the one adjacent second cup-shaped component, and
the first internal surface of each first cup-shaped component is in contact with the second external surface of the other adjacent second cup-shaped component.

7. The method according to claim 1, wherein:
a conductive material is supplied between the first external surface of each of the first cup-shaped components and the second internal surface of the one adjacent second cup-shaped component, and
a conductive material is supplied between the first internal surface of each of the first cup-shaped components and the second external surface of the other adjacent second cup-shaped component.

8. The method according to claim 1, wherein the following relationships are satisfied:

$10° \leq \theta_1 \leq 60°$, $10° \leq \theta_2 \leq 60°$, and $\theta_1 = \theta_2$, where, $\theta_1$ represents an angle formed by the internal surface of each of the first cup-shaped components and the axial direction of the first cup-shaped component, and $\theta_2$ represents an angle formed by the internal surface of each of the second cup-shaped components and the axial direction of the second cup-shaped component.

9. The method according to claim 1, wherein:

the gas to be detected is hydrogen, the catalyst layer includes platinum or palladium, and an electrical insulation layer is interposed between the internal surface of the internal through-hole and the catalyst layer.

10. The method according to claim 1, wherein:

the gas to be detected is hydrogen, and the catalyst layer includes ceramic containing platinum or palladium.

11. The method according to claim 10, wherein the ceramic is made of alumina.

12. The method according to claim 1, wherein:

the gas to be detected is CO or $NO_x$, and the catalyst layer includes ceramic containing platinum or palladium.

13. The method according to claim 12, wherein the ceramic includes tin oxide or zirconia.

14. The method according to claim 1, wherein a groove is formed in the pipe-shaped thermoelectric power generation device along the axial direction.

\* \* \* \* \*